United States Patent [19]

Lin

[11] 4,190,609

[45] * Feb. 26, 1980

[54] PROCESS FOR THE DIRECTED CHLORINATION OF XYLENES

[75] Inventor: Henry C. Lin, Grand Island, N.Y.

[73] Assignee: Hooker Chemicals & Plastics Corp., Niagara Falls, N.Y.

[*] Notice: The portion of the term of this patent subsequent to Jan. 17, 1995, has been disclaimed.

[21] Appl. No.: 866,136

[22] Filed: Dec. 30, 1977

Related U.S. Application Data

[63] Continuation-in-part of Ser. No. 729,439, Oct. 4, 1976, Pat. No. 4,069,264.

[51] Int. Cl.$^2$ .............................................. C07C 25/04
[52] U.S. Cl. ........................... 260/650 R; 252/429 R
[58] Field of Search ..................................... 260/650 R

[56] References Cited

U.S. PATENT DOCUMENTS

| | | | |
|---|---|---|---|
| 4,024,198 | 5/1977 | Buckholtz et al. | 260/650 R |
| 4,031,142 | 6/1977 | Graham | 260/650 R |
| 4,031,147 | 6/1977 | Graham | 260/650 R |
| 4,069,263 | 1/1978 | Lin | 260/650 R |
| 4,069,264 | 1/1978 | Lin | 260/650 R |

FOREIGN PATENT DOCUMENTS 952344  11/1956  German Democratic Rep. ..... 260/650 R Primary Examiner—Delbert E. Gantz
Assistant Examiner—Joseph A. Boska
Attorney, Agent, or Firm—Peter F. Casella; William J. Crossetta, Jr.; Arthur S. Cookfair

[57] ABSTRACT

A process for the production of nuclear chlorinated alkylbenzenes comprises reacting xylene with chlorine in the presence of a Lewis acid catalyst and a co-catalyst comprising a thianthrene compound or a mixture of thianthrene compounds characterized by the formula:

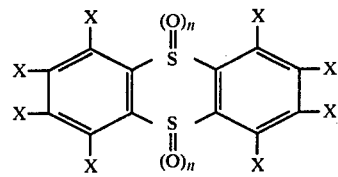

where n is 0 to 1, and each X is independently hydrogen, an electron-withdrawing substituent or an electron-donating substituent with the proviso that the total number of electron-donating substituents is no more than four; the total number of electron-withdrawing substituents is at least one and no more than seven; no more than three electron-donating substituents are present at the peri-positions; and when no electron-donating substituents are present on the thianthrene nucleus, at least one electron-withdrawing substituent is present at a peri-position.

The process is particularly useful in the preparation of 4-chloro-o-xylene and 4-chloro-m-xylene from o-xylene and m-xylene respectively.

21 Claims, No Drawings

PROCESS FOR THE DIRECTED CHLORINATION OF XYLENES

This application is a continuation-in-part of copending application Ser. No. 729,439, filed Oct. 4, 1976, now U.S. Pat. No. 4,069,264, and copending application Ser. No. 756,449, filed Jan. 3, 1977, now U.S. Pat. No. 4,069,263.

BACKGROUND OF THE INVENTION

This invention relates to a process for the nuclear chlorination of alkylbenzenes and, in particular, for the directed nuclear chlorination of xylene, especially o-xylene and m-xylene.

The chemical reaction of chlorine with alkylbenzenes, such as xylene or toluene, or the like to prepare nuclear substituted chloro-compounds such as monochloroxylene or monochlorotoluene, is well known and of considerable commercial importance. Such reactions are generally carried out in the presence of a chlorination catalyst such as antimony chloride, ferric chloride, aluminum chloride, and the like. The usual products of such reactions are a mixture of various monochlorinated and/or polychlorinated compounds and various positional isomers of these. For example, in the liquid phase substitution-chlorination of toluene, by reaction of chlorine and toluene, to form monochlorotoluene, the usual product is a mixture of orthochlorotoluene and parachlorotoluene which may, in addition, contain varying amounts of other chlorinated products. Of the major reaction products, that is orthochlorotoluene and parachlorotoluene, the latter is the most commercially valuable. In the past, considerable effort has been expended in attempts to direct the chlorination reaction in such a manner as to lower the ratio of orthochlorotoluene to parachlorotoluene, that is, to discover reaction conditions under which the formation of parachlorotoluene is favored. Similarly, in the nuclear chlorination of xylene, the reaction product is typically a mixture of chloroxylene compounds and/or positional isomers. Thus, for example, in the chlorination of o-xylene, to form monochloroxylene, the usual product is a mixture of 4-chloro-o-xylene and 3-chloro-o-xylene. When the reaction of chlorine and o-xylene is carried out in the presence of a ring chlorination catalyst, such as Fe, FeCl$_3$, SbCl$_5$, or the like, the monochlorinated reaction product is typically characterized by a ratio of 4-chloro-o-xylene:3-chloro-o-xylene of less than about 1.5:1. For some purposes the 4-chloro isomer is preferred over the 3-chloro-isomer, for example, as an intermediate in the preparation of insecticides. For this reason, efforts have been expended in attempts to direct the chlorination of o-xylene in such a manner as to increase the ratio of 4-chloro-o-xylene:3-chloro-o-xylene produced, that is, to discover reaction conditions or methods whereby the formation of 4-chloro-o-xylene is increased.

It is known from U.S. Pat. No. 1,946,040 that when alkylbenzenes are reacted with chlorine, the yield of parachlorinated product is improved with the aid of a mixed catalyst comprising sulfur and antimony trichloride and, optionally, iron or lead. In British Pat. No. 1,153,746 (1969) it is disclosed that in the chlorination of toluene in the presence of a ring chlorination catalyst, such as ferric chloride, antimony chloride, and the like, the ratio of orthochloro to parachloro isomers produced may be lowered by the presence of an organic sulfur compound such as thiophene, hexadecylmercaptan, dibenzothiophene or the like. Furthermore, in British Pat. No. 1,163,927 (1969) it is disclosed that the proportion of parachlorotoluene produced may be improved when toluene is chlorinated in the presence of elemental sulfur or an inorganic sulfur compound and a ring-chlorination catalyst such as ferric chloride, aluminum chloride, antimony chloride, zinc chloride, iodine, molybdenum chloride, stannous chloride, zirconium tetrachloride or boron trifluoride. In U.S. Pat. No. 3,226,447, issued Dec. 28, 1965 to Bing et al, it is disclosed that in the substitution-chlorination of benzene and toluene, the ratio of ortho isomer to para isomer in the chlorinated product may be lowered when the reaction is carried out in the presence of an iron, aluminum or antimony halide catalyst and a co-catalyst which is an organic sulfur compound wherein the sulfur is divalent. Examples of such co-catalyst include various mercaptans, mercapto-aliphatic carboxylic acids, aliphatic thiocarboxylic acids, alkyl sulfides, alkyl disulfides, thiophenols, aryl sulfides, aryl disulfides and the like containing divalent sulfur. The use of such co-catalysts in the chlorination of toluene produces a product wherein the ratio of orthochlorotoluene to parachlorotoluene is 1.2, indicating a considerable improvement over the ortho to para isomer ratio achieved in the absence of the co-catalyst. However, it will be apparent that even a 1.2 ratio of ortho to para isomer represents a considerable economic disadvantage in the production of substantial amounts—greater than 50 percent of the monochlorotoluene mixture—of the unwanted ortho isomer. Thus, it will be apparent that a considerable commercial benefit is to be derived from a still further lowering of the ortho to para isomer ratio.

Still further improvements in the preparation of monochloroalkylbenzenes wherein para-chloro isomer production is favored, are disclosed in U.S. Pat. Nos. 4,031,142 and 4,031,147. U.S. Pat. No. 4,031,142 discloses a process for the preparation of nuclear chlorinated alkylbenzenes, such as monochlorotoluene which comprises reacting an alkyl-benzene, such as toluene, with chlorine in the presence of a Lewis acid catalyst and, as a co-catalyst, thianthrene. When alkylbenzenes are chlorinated in accordance with the process of U.S. Pat. No. 4,031,142, the formation of parachloro-isomers is favored. In accordance with U.S. Pat. No. 4,031,147, the formation of parachloroalkylbenzenes is favored when alkylbenzenes are reacted with chlorine in the presence of a Lewis acid catalyst and a co-catalyst comprising a thianthrene compound or mixture of thianthrene compounds characterized by the formula:

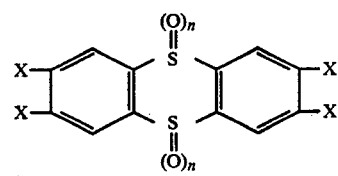

where each n is 0 to 1, and each x is hydrogen or an electron-withdrawing substituent. Although the processes of the prior art provide improvements in the preparation of parachloroalkylbenzenes, it will be apparent that still further improvements, especially in the preparation of parachloroxylenes, would be desirable and of commercial benefit.

It is an object of the present invention to provide an improved process for the directed nuclear chlorination of aromatic compounds. It is a further object to provide a process for the directed nuclear chlorination of alkyl-benzenes, especially xylene, whereby the chlorinated product is characterized by a desirably high ratio of parachloro or 4-chloro-, to other monochloroisomers. It is a still further object to provide an improved para-directing co-catalyst for such processes. It is a still further object to provide a novel catalyst system based on a para-directing co-catalyst comprising a thianthrene compound or mixture of thanthrene compounds, having both electron-withdrawing substituents and electron-donating substituents on the nucleus thereof.

The thianthrene compounds employed as para-directing co-catalysts in accordance with this invention are described hereinbelow in accordance with the current Chemical Abstracts system whereby the numbering of ring positions is as follows:

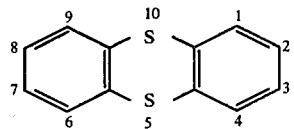

SUMMARY OF THE INVENTION

In accordance with this invention there is provided a process for the directed nuclear chlorination of xylene which comprises reacting xylene with chlorine in the presence of a Lewis acid catalyst and a co-catalyst comprising a thianthrene compound or a mixture of thianthrene compounds characterized by the formula:

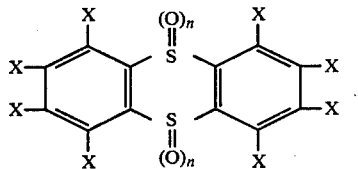

where n is 0 to 1, and each X is independently hydrogen, an electron-withdrawing substituent or an electron-donating substituent with the proviso that the total number of electron-donating substituents is no more than four; the total number of electron-withdrawing substituents is at least one and no more than seven; no more than three electron-donating substituents are present at the peri-positions; and when no electron-donating substituents are present on the thianthrene nucleus, at least one electron-withdrawing substituent is present at a peri-position.

The process of this invention is particularly directed to the chlorination of o-xylene and m-xylene. It has been found that when o-xylene is chlorinated in accordance with this invention, utilizing the substituted thianthrene co-catalysts disclosed herein, the formation of 4-chloro-o-xylene is favored, and the reaction product is characterized by a high ratio of 4-chloro-o-xylene:3-chloro-o-xylene. When m-xylene is chlorinated in accordance with this invention, the formation of 4-chloro-m-xylene is favored and a substantial increase is achieved in the ratio of 4-chloro-m-xylene:2-chloro-m-xylene in the reaction product.

The co-catalysts suitable for use in the process of this invention are characterized by the formula shown hereinabove and include, for example, thianthrene compounds, as well as the analogous mono- or di-sulfoxide compounds, wherein one or more electron-withdrawing substituents and one or more electron-donating substituents are present in the positions designated, as well as mixtures of such compounds. When more than one electron-donating substituent is present on the thianthrene nucleus, the substituents may be the same or different. Suitable electron-donating substituents include, for example, alkyl and akloxy groups. Preferably the electron-donating substituents are lower alkyl or alkoxy of 1 to 12 carbon atoms, and most preferably, methyl. When more than one electron-withdrawing substituent is present on the thanthrene nucleus, the substituents may be the same or different. Suitable electron-withdrawing substituents which may be present on the thianthrene or thianthrene oxide nucleus include for example, halo-, alkanoyl-, nitro-, sulfonyl-, cyano-, quarternary amino-, trifluoromethyl groups and the like, the preferred electron-withdrawing substituents being chloro-, fluoro-, bromo-, acetyl-, benzoyl, and trifluoromethyl and most preferably, chloro-.

The para-directing co-catalysts of the present invention differ substantially from the thianthrene co-catalysts of the prior art in that at least one electron-donating substituent is present on the thianthrene nucleus and/or that an electron-donating substituent or an electron-withdrawing substituent is present at one or more of the peri-positions. Prior to the present invention it was considered that the presence of an electron-donating substituent on the thianthrene nucleus would be disadvantageous and would most likely diminish or negate the para-directing catalytic effect. Methyl-thianthrenes, such as 2,3,7,8-tetramethylthianthrene have been found to be substantially ineffective as para-directing co-catalysts when employed with a Lewis acid catalyst in the chlorination of alkyl-benzenes. Furthermore, prior to the present invention, it was considered that the presence of a substituent other than hydrogen at the peri-position of the thianthrene nucleus, that is, positions 1,4,6 and 9, adjacent to the sulfur atoms, would inhibit or lessen the para-directing effect of the thianthrene compound. It is surprising therefore, in accordance with this invention, to find that the para-directing catalytic activity of a thianthrene compound may actually be enhanced by the presence of one or more electron-donating substituents, such as methyl substituents, and by the presence of either an electron-withdrawing substituent or an electron-donating substituent at one or more of the peri-positions of judiciously selected thianthrene compounds.

The preferred co-catalysts of this invention are the thianthrene compounds and mixtures thereof characterized by the formula shown hereinabove when n is 0, and two methyl groups and two to six chlorine atoms are present on the thianthrene nucleus in the positions designated. Most preferred are the dimethylhexachlorothianthrenes, dimethylpentachlorothianthrenes and dimethyltetrachlorothianthrenes and mixtures thereof. Also preferred as co-catalysts are the 1,4,6,9-tetrahalothianthrenes, especially 1,4,6,9-tetrafluorothianthrene, the latter being a heretofore unknown compound.

The thianthrene compounds employed as co-catalyst in accordance with this invention may be prepared by reacting an appropriately substituted benzene compound with sulfur monochloride in the presence of aluminum chloride. The resultant substituted thianthrene compound may be further substituted, as desired, for example by chlorination. The substituted benzene starting compound may be selected on the basis of the substituents desired in the final thianthrene product. Thus for example, an excess of orthochlorotoluene may be reacted with sulfur monochloride (as the limiting reactant) in the presence of aluminum chloride (typically in a molar ratio of $AlCl_3:S_2Cl_2$ of about 0.8:1.0) at a temperature of about 50° Celsius to produce dimethyldichlorothianthrene as a mixture of 2.7-dimethyl-3,8-dichloro-, and 2,8-dimethyl-3,7-dichloro-isomers. The product may then be further reacted for example with chlorine in situ or in a solvent such as nitrobenzene to produce such derivatives as dimethyltetrachlorothianthrene, dimethylpentachlorothianthrene and dimethylhexachlorothianthrene. In a similar manner, various other appropriately substituted benzene compounds may be employed as starting materials to prepare other substituted thianthrene compounds useful as co-catalysts in the process of this invention. In some instances the thianthrene compounds prepared are mixtures predominantly composed of thianthrene compounds or isomers characterized by the formula shown hereinabove. Such mixtures may be separated and the pure compounds employed as co-catalysts in accordance with this invention. However, in instances where the thianthrene compounds are prepared as mixtures, it has been found convenient and effective to employ the mixture as a co-catalyst without the need for separation into individual components.

An alternative method for the preparation of thianthrene co-catalysts of this invention is disclosed in co-pending application Ser. No. 822,181, filed Aug. 5, 1977. The process disclosed therein comprises adding sulfur monochloride to an excess of a selected substituted benzene compound in the presence of aluminum chloride and treating the resulting thianthrene compound:aluminum chloride complex with an alcohol to free the thianthrene compound and dissolve the aluminum chloride.

A wide variety of known Lewis acid catalysts may be employed in the process of the present invention. The term "Lewis acid catalyst" as employed herein includes, in addition to Lewis acids, those compounds or elements that will form or function as Lewis acids under the conditions of the chlorination reaction. Preferred catalysts for this purpose are compounds of antimony, lead, iron, molybdenum and aluminum, including for example, the halides, oxyhalides, oxides, sulfides, sulfates, carbonyls and elemental form of these elements and mixtures of such compounds and most preferably the chlorides, oxychlorides, oxides and elemental forms of antimony and iron. Typical of the catalysts which may be employed in the process of this invention are aluminum chloride, antimony trichloride, antimony pentachloride, antimony trioxide, antimony tetraoxide, antimony pentaoxide, antimony trifluoride, antimony oxychloride, molybdenum hexacarbonyl, lead sulfide, ferric chloride, ferrous chloride, ferrous sulfate, ferric oxide, ferrous sulfide, iron disulfide, iron pentacarbonyl, iron metal, and the like.

The amounts of catalyst and co-catalyst employed may vary considerably. Substantial benefits in terms of the increase in the proportion of 4-chloro-o-xylene isomer in the product may be achieved, for example, when the catalyst and co-catalyst are present in a total amount ranging from less than about 0.01 percent to about five percent by weight or more, based on the weight of xylene, and preferably in a molar ratio of catalyst:co-catalyst of about 0.01:1 to about 10:1. However, based on effectiveness as well as economic considerations, it is preferred to employ the catalyst and co-catalyst in a total amount of about 0.01 to about 2.0 weight percent, based on the weight of xylene and in a molar ratio of catalyst:co-catalyst of less than about 4:1 and most preferably about 0.10:1 to about 1:1.

Under atmospheric pressure, the chlorination reaction of the present invention may be carried out over a wide range of temperatures, ranging for example from sub-zero temperatures such as $-30°$ Celsius or below to over 100° Celsius. The upper limit of temperature is, of course, determined by the boiling point of the reaction mixture, and may, depending on the boiling point limitation, range as high as 150° Celsius or higher. However, no practical advantage is gained through the use of higher temperatures or extremely low temperatures, and it is preferred to utilize temperatures in the range of about $-20°$ to about 110° Celsius, and most preferably in the range of about 0° to about 70° Celsius. The optimum temperature will vary somewhat, depending on the particular catalyst system employed.

Although it is preferred to carry out the process at atmospheric presures, subatmospheric or superatmospheric pressures may be employed if desired.

The process of this invention may be carried out by chlorination of xylene in solution or in the absence of a solvent. Suitable solvents which may be employed, if desired, include for example various halogenated solvents such as carbon tetrachloride, or aromatic solvents such as monochlorobenzene. It is preferred, however, to carry out the chlorination directly, in the absence of a solvent.

The following specific examples are provided to further illustrate this invention and the manner in which it may be carried out. It will be understood, however, that the specific details given in the examples have been chosen for purpose of illustration and are not to be construed as a limitation of the invention. Those examples designated by the letter "C" are provided for comparative purposes. In the examples, unless otherwise indicated, all parts and percentages are by weight and all temperatures are in degrees Celsius. Product analyses were obtained using gas chromatographic techniques.

EXAMPLE 1

A mixture of 100 parts of o-xylene, 0.02 parts of $FeCl_3$ and 0.1 parts of a co-catalyst mixture of 11.48% dimethyltrichlorothianthrene and 88.52% dimethyltetrachlorothianthrene was cooled to 0° C. with stirring, and maintained thereat for a period of 4 hours while 100 parts of chlorine gas was slowly added. The reaction mixture was then quenched with water, extracted with ether, washed with aqueous sodium bicarbonate, and dried over anhydrous magnesium sulfate. Gas liquid chromatographic analysis of the reaction product indicated 1.28% o-xylene, 18.82% 3-chloro-o-xylene, 71.70% 4-chloro-o-xylene, and 8.20% dichloro-o-xylene. The ratio 4-chloro-o-xylene:3-chloro-o-xylene was 3.81.

EXAMPLE 2C

For purposes of comparison, the procedure of Example 1 except that the methylchlorothianthrene co-catalyst was admitted and 0.1 part of $FeCl_3$ was employed as the sole catalyst. Gas liquid chromatographic analysis of the reaction product indicated 10.42% o-xylene, 34.96% 3-chloro-o-xylene, 48.24% 4-chloro-o-xylene and 6.38% dichloro-o-xylene. The ratio of 4-chloro-o-xylene:3-chloro-o-xylene was 1.38.

EXAMPLE 3

A mixture of 100 parts of m-xylene, 0.02 parts of $FeCl_3$ and 0.1 parts of a co-catalyst mixture of 5.19% dimethyltetrachlorothianthrene, 58.83% dimethylpentachlorothianthrene and 32.33% dimethylhexachlorothianthrene was cooled to 0° C. with stirring and maintained thereat for a period of about 4 hours while 100 parts of chlorine gas was passed into the mixture. The reaction mixture was quenched with water, extracted with ether, washed with aqueous sodium bicarbonate, and dried over anhydrous magnesium sulfate. Gas liquid chromatographic analysis of the reaction product indicated 2.56% m-xylene, 21.09% 2-chloro-m-xylene, and 76.35% 4-chloro-m-xylene.

EXAMPLES 4–12

The Examples of Table I were carried out following a procedure essentially similar to that of Example 1, except the catalyst, co-catalyst, and reaction temperature were varied as shown.

TABLE I

| EX. | CATA-LYST | CO-CATALYST | REACTION TEMPERATURE (°C.) | O-XYLENE | 3-CHLORO-O-XYLENE | 4-CHLORO-O-XYLENE | DICHLORO-O-XYLENE | ISOMER RATIO 4-CHLORO:3-CHLORO |
|---|---|---|---|---|---|---|---|---|
| 4 | $FeCl_3$ | I | 50° | 51.38 | 14.46 | 30.79 | 3.37 | 2.13 |
| 5 C | $FeCl_3$ | Thianthrene | 50° | 43.39 | 23.60 | 29.03 | 3.98 | 1.23 |
| 6 | Fe | II | 0° | 3.28 | 22.31 | 67.81 | 6.60 | 3.04 |
| 7 | Fe | II | 50° | 0.32 | 23.65 | 65.28 | 10.75 | 2.76 |
| 8 | $SbCl_5$ | II | 0° | 3.07 | 23.72 | 65.69 | 7.52 | 2.77 |
| 9 | $SbCl_5$ | III | 0° | 8.51 | 21.69 | 62.47 | 7.33 | 2.88 |
| 10 | $SbCl_5$ | IV | 0° | 9.98 | 25.10 | 60.50 | 4.42 | 2.41 |
| 11 C | $SbCl_5$ | Thianthrene | 0° | 2.21 | 35.15 | 56.95 | 5.69 | 1.62 |
| 12 C | $SbCl_5$ | None | 0° | 9.06 | 34.13 | 49.14 | 7.67 | 1.44 |

CO-CATALYST:
I. dimethyldichlorothianthrene
II. a mixture of 5.19% dimethyltetrachlorothianthrene, 58.83% dimethylpentachlorothianthrene and 32.33% dimethylhexachlorothianthrene.
III. a mixture of 11.48% dimethyltrichlorothianthrene and 88.52% dimethyltetrachlorothianthrene.
IV. peri-tetrafluorothianthrene

What is claimed is:

1. A process for the nuclear chlorination of xylene comprises reacting ortho-xylene or meta-xylene with chlorine in the presence of a Lewis acid catalyst and a co-catalyst comprising a thianthrene compound or a mixture of thianthrene compounds characterized by the formula:

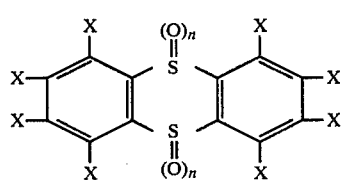

where n is 0 to 1, and each X is independently hydrogen, an electron-withdrawing substituent or an electron-donating substituent with the proviso that the total number of electron donating substituents is at least one and no more than four; the total number of electron-withdrawing substituents is at least one and no more than seven; no more than three electron-donating substituents are present at the peri-positions.

2. A process according to claim 1 wherein said electron-withdrawing substituent is selected from the group consisting of fluoro-, chloro-, bromo-, acetyl-, benzoyl-, and trifluoromethyl.

3. A process according to claim 2 wherein said electron-donating substituent is an alkyl or alkoxy substituent.

4. A process according to claim 3 wherein the Lewis acid catalyst is a halide, oxyhalide, oxide, sulfide, sulfate, carbonyl or elemental form of antimony, lead, iron, molybdenum, or aluminum.

5. A process according to claim 4 wherein the co-catalyst is a thianthrene compound or mixture of thianthrene compounds characterized by the formula shown wherein each n is 0.

6. A process according to claim 5 wherein the co-catalyst is a thianthrene compound or mixture of thianthrene compounds characterized by the formula shown wherein at least one x is an electron-donating substituent selected from a lower alkyl and lower alkoxy of 1 to 12 carbon atoms.

7. A process according to claim 6 wherein the Lewis acid catalyst is a chloride, oxychloride or elemental form of antimony or iron.

8. A process according to claim 7 wherein the co-catalyst is a thianthrene compound or mixture of thianthrene compounds characterized by the formula shown wherein the electron-withdrawing substituent is chloro-.

9. A process according to claim 8 wherein the co-catalyst is a thianthrene compound or mixture of thianthrene compounds characterized by the formula shown wherein at least one x is methyl.

10. A process according to claim 6 wherein the co-catalyst is a substituted thianthrene compound or mixture of substituted thianthrene compounds having two methyl substituents and two to six chloro-substituents.

11. A process according to claim 10 wherein the Lewis acid catalyst is a chloride, oxychloride, or elemental form of antimony or iron.

12. A process according to claim 11 wherein the xylene is o-xylene.

13. A process according to claim 11 wherein the xylene is m-xylene.

14. A process according to claim 11 wherein the co-catalyst is dimethyldichlorothianthrene.

15. A process according to claim 11 wherein the co-catalyst is a mixture of chloro-substituted dimethylthianthrenes wherein the number of chloro-substituents is from about two to about 6.

16. A process according to claim 5 wherein the co-catalyst is 1,4,6,9-tetrafluorothianthrene.

17. A process according to claim 15 wherein the Lewis acid catalyst is FeCl$_3$.

18. A process according to claim 15 wherein the Lewis acid catalyst is Fe.

19. A process according to claim 15 wherein the Lewis acid catalyst is SbCl$_5$.

20. A process for the preparation of monochloroxylene which comprises reacting a xylene compound selected from the group consisting of o-xylene and m-xylene, with chlorine at a temperature of about −20° to about 110° Celsius, in the presence of a catalyst system comprising a Lewis acid catalyst selected from the group consisting of chlorides oxychlorides oxides and elemental forms of antimony and iron; and a co-catalyst comprising a thianthrene compound or mixture of thianthrene compounds characterized by the formula:

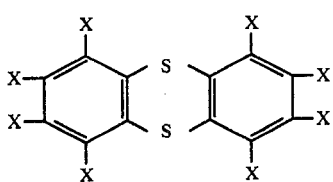

wherein each x is independently hydrogen, methyl, or an electron-withdrawing substituent selected from the group consisting of fluoro-, chloro-, bromo-, and trifluoromethyl-, with the proviso that two x's are methyl, and at least two x's are electron-withdrawing substituents.

21. A process according to claim 20 wherein the catalyst system comprises about 0.01 to about 5 percent by weight, based on the amount of xylene in a ratio of catalyst:co-catalyst of about 0.01:1 to about 10:1.

* * * * *